United States Patent [19]

Imai et al.

[11] 4,393,434

[45] Jul. 12, 1983

[54] CAPACITANCE HUMIDITY SENSOR

[75] Inventors: Yoshio Imai, No. 3-36-3, Horinouchi, Suginami-Ku, Tokyo; Yoichi Nabeta, Machida; Tadao Inuzuka, Kawasaki, all of Japan

[73] Assignee: Yoshio Imai, Tokyo, Japan

[21] Appl. No.: 323,586

[22] Filed: Nov. 20, 1981

[30] Foreign Application Priority Data

Dec. 16, 1980 [JP] Japan .................. 55-176504

[51] Int. Cl.³ .............................................. H01G 7/00
[52] U.S. Cl. .................................... 361/286; 73/336.5
[58] Field of Search ....................... 361/286; 73/336.5; 427/290, 38, 39; 219/121 PD

[56] References Cited

U.S. PATENT DOCUMENTS 2,690,403  9/1954  Gutzeit .
3,350,941 11/1967  Misevich et al. .
3,492,152  1/1970  Cariou .
4,151,034  4/1979  Yamamoto ................. 219/121 PD

FOREIGN PATENT DOCUMENTS 49-74588  7/1974  Japan .
52-12497  1/1977  Japan .
 53-9595  1/1978  Japan .
55-66749  5/1980  Japan .

*Primary Examiner*—Elliot A. Goldberg
*Attorney, Agent, or Firm*—Young & Thompson

[57] ABSTRACT

A capacitance humidity sensor according to the disclosure a non-conductive base plate, electrodes oppositely arranged on the base plate, a metal compound membrane formed by ion-plating independently on the electrodes, the metal compound membrane being roughened on its surface by plasma etching and being active to the humidity, and a moisture permeable metal skin formed on the metal compound membrane. The metal compound is preferably an oxide or nitride of aluminum or magnesium.

5 Claims, 3 Drawing Figures

CAPACITANCE HUMIDITY SENSOR

FIELD OF THE INVENTION

This invention relates to a capacitance humidity sensor, more particularly to a capacitance humidity sensor which is excellent in mechanical strength but does not degrade its performance in a high temperature and organic solvent atmosphere and exhibits a quick response and provides an accurate measurement of humidity.

BACKGROUND OF THE INVENTION

In general, it is understood that an electrical humidity sensor is a kind of transducer for indicating as relative humidity a change in electrical properties depending on a change in humidity condition, which is classified into two wide categories in basic principle, one of which utilizes a change in electric resistance and the other of which measures a change in electrostatic capacitance. The latter capacitance type, namely a type of humidity sensor which determines humidity by measurement of capacitance variation upon absorption of moisture into a humidity sensing element, has heretofore employed a porcelain plate or specially fabricated glass fibres or alumite sheet as a dielectric element, which is poor in sensitivity and thus has a practical problem. Furthermore, a humidity sensor has been recently proposed which utilizes a polymeric membrane as the dielectric element for functioning as a sensing part, as disclosed for example, in the Japanese Opened Application 74588/74, the Japanese Opened Application 66749/80 and the U.S. Pat. No. 3,350,941.

In general, when the dielectric element comprising the polymeric membrane is used as the humidity sensing layer, the dielectric element is excellent in responsiveness to the humidity and shows a good reproducibility. Furthermore, it has the advantage that a relationship between the humidity and the capacitance is quite linear, improving the measuring accuracy. On the other hand, however, the dielectric polymeric membrane has the disadvantage that it can be stripped off from a base plate upon a long period of exposure to an excessively dry or a high humidity condition, resulting in degradation of its humidity sensing property. In addition, the polymeric membrane has a further disadvantage in that it is susceptible to corrosion with organic solvents (such as acetone) so that it may not be used in an atmosphere of much organic solvent vapor, such as in a printing factory, paint factory or the like because of its adverse effect.

Thus, there has still been desired a practical capacitance humidity sensor in the art, which may be advantageously used in a harmful atmosphere, such as a high temperature and an organic solvent atmosphere, and is excellent in mechanical strength. For this requirement, there have been proposed, for example, "a humidity sensing element of metal oxide membrane" (the Japanese Opened Application 12497/77) and "a humidity detecting element using an anodic oxide membrane of aluminium" (the Japanese Opened Application 9595/78). Both of these utilize a technique of forming a conductive porous metal oxide membrane on a base plate of aluminum or the like by means of electrolysis or otherwise, which provides a rough surface of the element leading to an error of measurement, as well as an unsatisfactory mechanical strength of the metal oxide membrane itself, and thus cannot meet the requirement described hereinbefore.

Now it has been found out that instead of forming the membrane on the base plate through oxidation or electrolysis, a formation of a metal oxide membrane (such as metal oxide or nitride) on an insulating base plate, such as a glass plate or the like which is inert to oxidation, through the ion-plating technique of introducing the corresponding metal vapor and oxygen, nitrogen or ammonia gas into a high frequency field may provide a metal oxide membrane of extremely high strength, which may be well used in the severe environment described hereinabove. Furthermore, it has been found that a mechanical treatment of the metal oxide, such as a roughening treatment of its surface through plasma etching, may provide excellent responsiveness and reproducibility, as well as an improvement in accuracy of measurement.

SUMMARY OF THE INVENTION

Accordingly, a general object of the invention is to provide a capacitance humidity sensor which is excellent in mechanical strength, highly resistant to degradation of performance even under severe conditions of high temperature and organic solvent atmosphere and permits very quick response as well as accurate measurement of humidity.

A principal object of the invention is to provide a capacitance humidity sensor which comprises a non-conductive base plate, electrodes oppositely arranged on the base plate, a metal compound membrane formed independently on the electrodes, said metal compound membrane being active to the humidity, and a moisture permeable metal skin formed on the metal compound membrane.

PREFERRED EMBODIMENT OF THE INVENTION

In accordance with the capacitance humidity sensor of the invention, it is preferred to roughen the metal compound membrane at its surface by the mechanical treatment, such as plasma etching. Furthermore, the metal compound membrane is formed on the base plate by the ion-plating technique preferably using a high frequency source. Thus, the humidity sensor according to the invention may be prepared by applying a high voltage to a non-conductive base plate with oppositely arranged electrodes thereon while holding the same on a high voltage electrode in a vacuum generating chamber, evacuating impure gases within the chamber to provide the high vacuum therein, introducing a selected gas from outside, generating a high frequency field in the chamber, heating and evaporating a metal specimen arranged in the chamber, reacting the evaporated metal specimen with the selected gas in the high frequency field to form a skin of metal compound independently on the non-conductive base plate, and roughening the surface of the skin through mechanical treatment, such as plasma etching.

Now the invention will be described in more detail for the best mode presently contemplated with reference to the accompanying drawings.

DETAILED DESCRIPTION OF THE INVENTION

Figure 1:
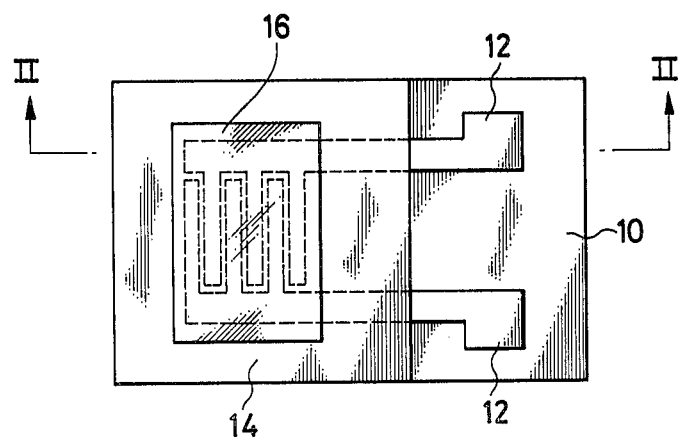
FIG. 1 is a plan view of the capacitance humidity sensor according to the invention.
Figure 2:
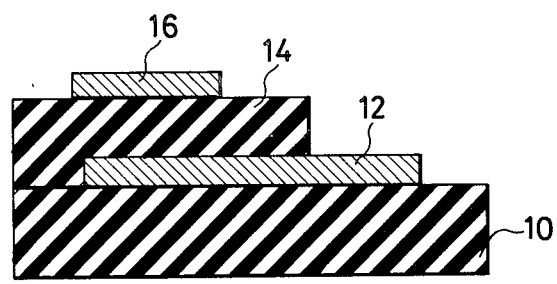
FIG. 2 is a sectional view of the capacitance humidity sensor taken along the line II—II of FIG. 1.
Figure 3:
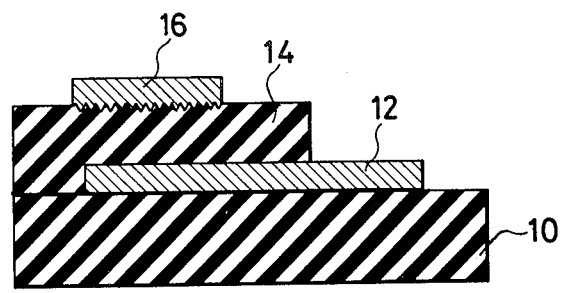
FIG. 3 is a sectional view of another embodiment of the capacitance humidity sensor, similar to FIG. 2.

FIGS. 1 and 2 illustrate one embodiment of the capacitance humidity sensor according to the invention, in which reference 10 shows a glass base plate cut to a size of about 5×8 mm. On the glass base plate 10 are formed oppositely a pair of lower electrodes 12, 12 as shown in FIG. 1 by means of deposition, photo-etching or the like. The lower electrodes 12, 12 are preferably formed into a comb shape and are arranged in such a manner that their comb teeth are meshed but not in contact with each other. A chemically inert material such as gold or platinum is suitably selected as the lower electrodes. On the base plate 10 with the lower electrodes 12, 12 thus oppositely arranged thereon is independently formed a metal compound membrane 14 active to the humidity such as a metal oxide or nitride membrane of a thickness of about 2 to 5μ using the ion-plating method with a high frequency source as described hereinafter. The membrane 14 is preferably subjected to mechanical treatment such as plasma etching for roughening its surface, as shown in FIG. 3. On the metal compound membrane 14 thus formed is then deposited a metal skin 16 such as a gold or platinum skin which is chemically stable but moisture permeable for forming an upper electrode 16 thereby providing the capacitance humidity sensor which is particularly excellent in mechanical strength and responsiveness.

Figure 4:
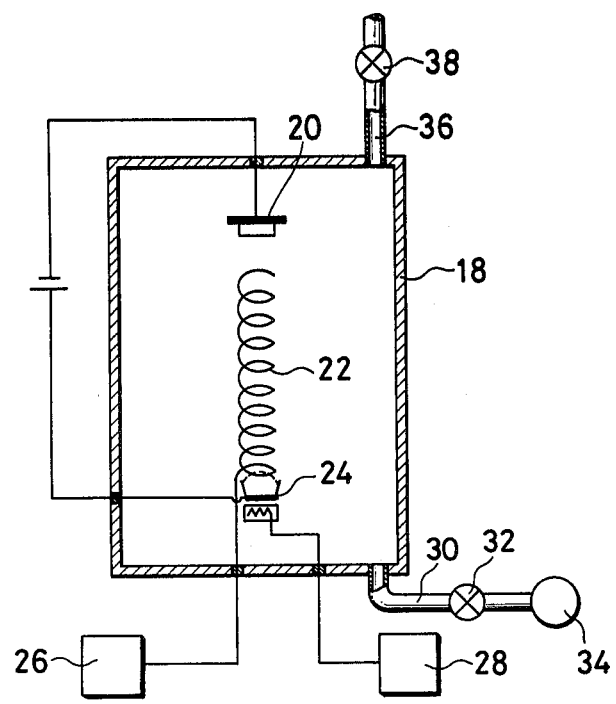
FIG. 4 is a schematic view illustrating the method of preparing the capacitance humidity sensor according to the invention.

A method for forming the metal compound membrane 14 on the base plate 10 with the oppositely arranged lower electrodes 12, 12 will be described hereinbelow. FIG. 4 shows an apparatus for conducting the method in which an electrode 20, a coil 22 and a heater 24 for positioning the metal specimen are arranged in a sealed vacuum chamber 18. A high voltage of direct current of 500 V to 1 KV is applied to the electrode 20 while the coil 22 is connected to an external high frequency source 26. The heater 24 which is provided for positioning and heating various metal specimen as described hereinafter is preferably formed as a tungsten tray and is connected to an external electric source 28 capable of supplying a current of 50 to 100 A at 50 V.

From the vacuum chamber 18 extends a pipe 30 which is connected to a vacuum pump 34 through a valve 32, while a pipe 38 also extends therefrom for connection to a gas source (not shown) through a valve 38.

In operation, the base plate 10 with the lower electrodes 12, 12 is horizontally secured under the electrode 20 in the vacuum chamber 18, while aluminum is placed on the heater 24. Then the vacuum chamber 18 is sealed and is then evacuated by the pump 34 for removing impure gases therefrom. When a vacuum of $10^{-5}$ to $10^{-4}$ torr is reached in the vacuum chamber 18, the valve 38 is opened for introducing a mixed gas of oxygen and argon in a ratio of 2:1 into the chamber 18 and thereby stabilizing the vacuum at $10^{-2}$ to $10^{-3}$ torr. Then the voltage of direct current of 500 V to 1 KV is applied to the electrode 20. On the other hand, the high frequency source of 13.65 MHz at 200 to 300 W is connected to the coil 22 while the current of 50 to 100 A at 5 V is passed through the heater 24 for heating and evaporating aluminium on the heater. The aluminium which has been heated and evaporated under vacuum passes through the high frequency field of the coil 22 and is concentrated onto the base plate 10 to which has been applied the high voltage by the electrode 20. The aluminium vapor is then reacted with the mixed gas to form an aluminium oxide skin on the base plate 10. The aluminum oxide skin is preferably formed to a thickness of 2 to 5μ, although the thickness may be controlled by adjusting the time of current flow to the heater 24, the amount of the metal specimen and the applied voltage applied to the electrode 20. Thereafter, the base plate 10 is removed from the vacuum chamber 18 and is subjected to the plasma etching in a conventional manner to roughen the surface 15 of the aluminium oxide skin (see FIG. 3). Preferably the surface is roughened to a depth of about 100 to 1000 Å, thereby enlarging the surface area and facilitating the reaction with moisture on the surface of the dielectric material. Thus, the quick responding sensor may be achieved. In this way, the moisture permeable upper metal electrode 16, such as a gold or platinum skin, is deposited after formation of the metal compound membrane 14 for providing the humidity sensor according to the invention.

The ion-plating in the high frequency field produces an extremely high bonding strength of aluminium oxide to the base plate 10 while the aluminium oxide is highly resistant to heat and acid, resulting in an excellent humidity sensor which may be well used under severe conditions such as in the high temperature and solvent vapor atmosphere. Although the metal oxide (such as aluminium oxide) has been exemplified in the ion-plating for the illustrated embodiment, a metal nitride skin may be similarly formed on the base plate by introducing an ammonia gas into the vacuum generating chamber in lieu of the mixed gas described hereinbefore. The metal nitride, similarly to the metal oxide, exhibits suitable properties for the humidity sensor. As the metal specimen, aluminium may be replaced by magnesium.

Figure 5:
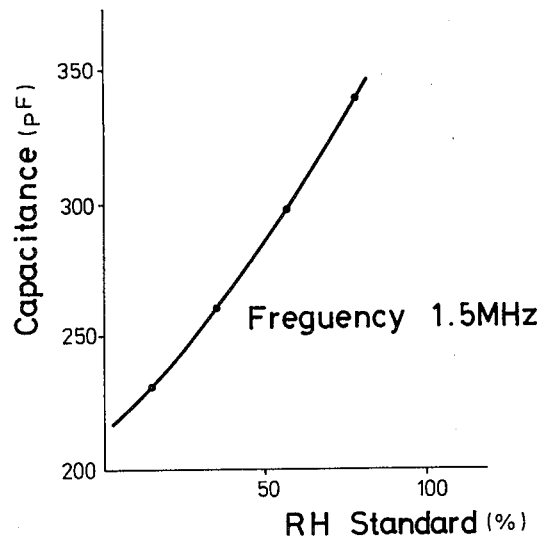
FIG. 5 is a graph showing the relationship between the relative humidity and the capacitance in the capacitance humidity sensor according to the invention.

The capacitance humidity sensor according to the invention shows an approximately linear proportional relationship between the relative humidity and the capacitance as in FIG. 5 showing the significant improvement in accuracy of measurement. In addition, the metal compound skin (including metal oxide and metal nitride skins) is firmly formed on the base plate thereby providing sufficient mechanical strength to be used under severe conditions. Particularly, utilization of the metal compound membrane in lieu of a polymeric membrane as the dielectric element allows the humidity sensor of the invention to be used for long periods without losing its sensing property in an atmosphere filled with organic solvent vapor but without aging. The humidity sensor according to the invention has the further advantages that soldering to the electrode may be facilitated due to the highly improved heat resistance and that the sensor itself may be dried by heating after the sensing element has absorbed excess moisture.

While there have been described what are at present considered to be the preferred embodiments of the invention, it will be obvious to those skilled in the art that various changes and modifications may be made without departing from the true spirit and scope of the invention.

What is claimed is:

1. A capacitance humidity sensor which comprises a non-conductive base plate, electrodes oppositely arranged on the base plate, a metal compound membrane formed by ion-plating independently on the electrodes, said metal compound membrane being roughened at its surface by plasma etching and being active to the humidity, and a moisture permeable metal skin formed on the roughened surface of the metal compound membrane.

2. The capacitance humidity sensor according to claim 1, wherein the non-conductive base plate is a glass plate.

3. The capacitance humidity sensor according to claim 1 wherein the metal compound membrane consists of metal oxide or nitride.

4. The capacitance humidity sensor according to claim 1, wherein the electrodes are formed in a comb shape and are arranged oppositely so as to mesh with but not contact with each other.

5. The capacitance humidity sensor according to claim 3, wherein the metal of the oxide or nitride is aluminum or magnesium.

* * * * *